(12) United States Patent
Goldowsky

(10) Patent No.: US 6,432,135 B1
(45) Date of Patent: Aug. 13, 2002

(54) TORSION HEART VALVE

(75) Inventor: Michael Philip Goldowsky, Valhalla, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/579,313

(22) Filed: May 25, 2000

Related U.S. Application Data
(60) Provisional application No. 60/136,064, filed on May 26, 1999.

(51) Int. Cl.[7] .............................. A61F 2/06; A61F 2/24
(52) U.S. Cl. .................. 623/2.21; 137/512.1; 137/527; 137/535
(58) Field of Search ......................... 623/2.1, 2.2, 2.22, 623/2.23, 2.24, 2.21; 251/305; 137/512.1, 527, 535

(56) References Cited

U.S. PATENT DOCUMENTS

| | | | | |
|---|---|---|---|---|
| 3,367,364 A | * | 2/1968 | Cruz, Jr. et al. | 137/527.8 |
| 3,370,305 A | * | 2/1968 | Goott et al. | 623/2.21 |
| 3,448,465 A | * | 6/1969 | Pierce et al. | 623/2.21 |
| 4,019,532 A | * | 4/1977 | Schittek | 137/527 |
| 4,643,732 A | * | 2/1987 | Pietsch et al. | 623/2 |
| 4,657,545 A | * | 4/1987 | Zibelin | 623/2 |
| 4,908,028 A | * | 3/1990 | Colon et al. | 623/2 |
| 4,967,778 A | * | 11/1990 | Ball et al. | 137/1 |
| 5,607,469 A | * | 3/1997 | Frey | 623/2 |
| 5,674,279 A | * | 10/1997 | Wright et al. | 623/2 |

\* cited by examiner

Primary Examiner—Paul B. Prebilic
Assistant Examiner—William H. Matthews
(74) Attorney, Agent, or Firm—Francis L. Conte

(57) ABSTRACT

A rigid leaflet blood check valve uses a torsion wire suspension to suspend the leaflet. The leaflet is non-contacting with the housing. Complete washout of all valve parts in blood contact exists. This eliminates areas of blood stasis which exist in valves employing conventional pivot bearings. Relative motion, wear, and washout problems have been eliminated in the valve.

20 Claims, 4 Drawing Sheets

TORSION HEART VALVE

This application claims the benefit of U.S. Provisional Application Serial No. 60/136,064, filed May 26, 1999.

BACKGROUND OF THE INVENTION

The present invention relates to fluid check valves, and, more specifically, to implantable heart valves that work in blood. Many heart valves in use today use rigid components because they last a long time with high mechanical reliability as opposed to pig valves which have limited life. A disadvantage in rigid valve technology even with the most hemocompatible materials, like carbon and titanium, is the problem of washing out the bearing pivots with fresh blood.

Typical pivots employ a male pin combined with a female socket machined into the housing of the valve. The pivot allows the leaflet to rotate in the housing either opening or closing the valve passageway. Since the female socket is counterbored into the wall of the housing, into which the male pivot sits, it is difficult to hydrodynamically flush out the bearing continuously with fresh blood. This inherent deficiency has existed in valve designs for decades.

The present invention eliminates these pivots and the associated washout problem. Without sufficient bearing washout, anti-coagulants must be taken by the patient to avoid clotting and thrombosis in the valve. Because this problem is eliminated in the present design, it may be possible to eliminate anti-coagulant therapy. This is a major advantage.

Another object of the present invention is to eliminate contact and wear as exists in pivot bearings for the leaflet. Hard ceramic carbon is used in existing valves not only because of its blood chemical compatibility, but because it is wear resistant to last for many years. The internal stops in the pivots are highly loaded so a wear resistant bearing surface is required.

In the instant invention, since no contact occurs in the bearing, highly wear resistant materials are not required. This allows the use of new and better valve materials in the future that are even more thrombo-resistant.

Another object of the invention is to eliminate stringent machining tolerances in the bearing parts. Conventional pivot bearing tolerances are so stringent that selective assembly of parts is employed to achieve the best fit possible. The present torsion wire suspension should not require such tight tolerances.

Accordingly, it is desired to provide a suspension for a leaf valve for eliminating bearing contact.

BRIEF SUMMARY OF THE INVENTION

A valve includes a housing, a valve leaflet disposed therein, and a torsion wire fixedly suspending the leaflet to the housing for pivotal reciprocation therein. Pivot bearings are thusly eliminated for supporting the valve leaflet, and when used as a prosthetic heart valve corresponding blood damage is also eliminated.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DETAILED DESCRIPTION OF THE INVENTION

Figure 1:
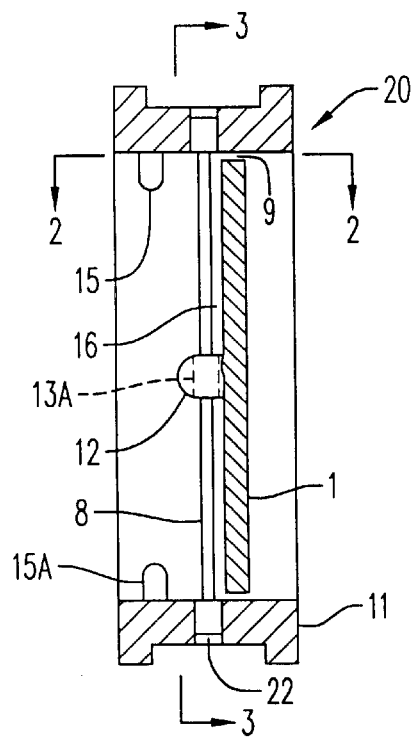
FIG. 1 is a sectional view along line 1—1 of FIG. 2 for a closed valve showing one leaflet in section and the leaflet suspension wire unsectioned.

Illustrated in FIG. 1 is an exemplary view through a prosthetic bi-leaflet heart valve 20 including two sets of a valve leaflet 1 suspended on a torsion wire 8 which is bonded into leaflet socket 12 at the center of the wire. The ends of the wire are terminated in outboard fittings 13 that are adhesively bonded into tubular valve housing 11 for effecting pivotal reciprocation of the leaflets 1 during operation in a heart. The inside diameter or surface of the housing is flush to the fittings thereby providing a smooth surface for washout by blood.

Figure 2:
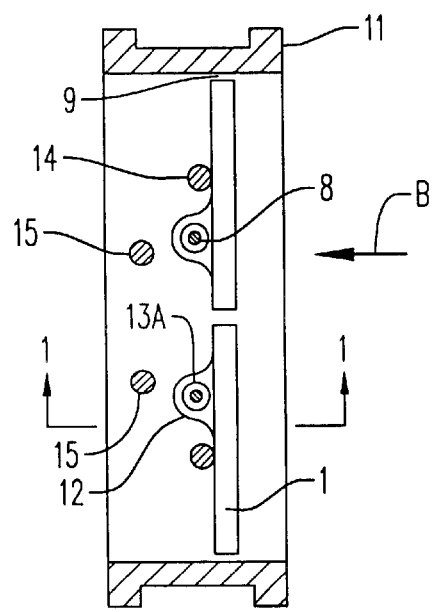
FIG. 2 is a partial sectional view along line 2—2 of FIG. 1 looking down upon the two closed leaflets. A bi-leaflet valve has been chosen here as a preferred embodiment. Closing pressure blood flow is arrow labeled B.

FIG. 2 shows a top view of FIG. 1 without the two leaflets in section. Wire 8 is seen in its cross section. The single inboard fitting 13A is located in the leaflet and bonded thereto, and centered between the two outboard fittings 13.

Figure 5:
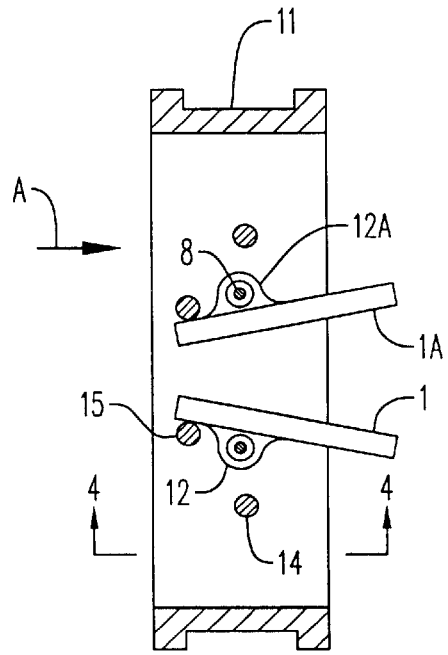
FIG. 5 is a partial section along line 5—5 of FIG. 4 showing the top view of the open leaflets and the leaflet stops. Fluid flow direction is arrow A.
Figure 6:
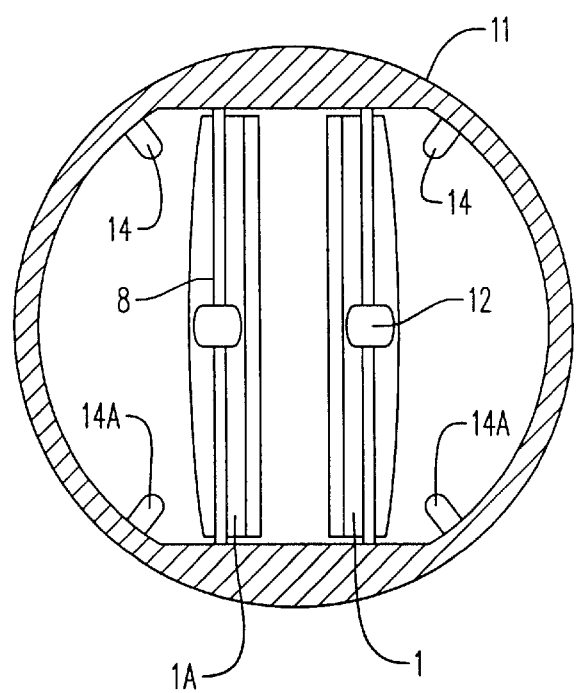
FIG. 6 is an end view of FIG. 4 along line 6—6 showing the housing in section and the leaflets not sectioned. Open pin stops are not shown for clarity.

Close stop pin 14 limits the leaflet positions when it is closed. Open stop 15 pin limits the valve leaflet position when it is open as shown in FIG. 5. Stops 15 at the top of the leaflet have symmetric counterpart pins 15A at the bottom of the leaflet. This is also true for stops 14 and 14A as shown in FIG. 3.

The line of centers between stops 14 and 14A is designed to pass through the centroid of the leaflet. In this way, the stops absorb the full pressure force on the leaflet without transmitting a load to the wire. This greatly reduces the maximum force on the wire for a closed leaflet.

Referring again to FIG. 1, the leaflet socket 12 is spaced from the leaflet to provide a gap 16 which is used to space the wire off the surface of the leaflet. Blood flows through this gap to wash out the wire environment surrounding it when the valve is open in FIG. 4.

Figure 3:
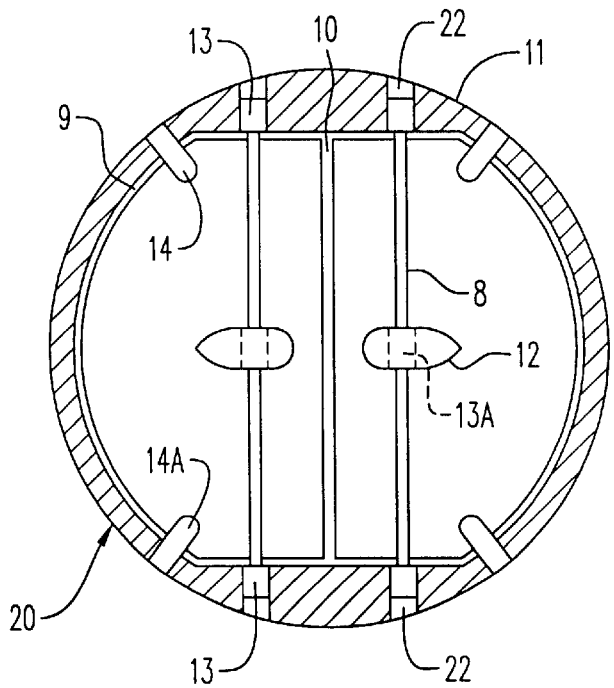
FIG. 3 is a view along line 3—3 of FIG. 1 showing the closed leaflets and the housing in section.

A gap 9 between the pair of leaflets and housing all around the leaflet perimeters in the common closed-leaflet plane shown in FIG. 3 ensures contactless operation of the leaflet. This gap is also washed out by blood flow as the leaflet rotates. This lack of leaflet contact with the housing ensures low blood damage as in conventional prosthetic heart valve designs.

However, the torsion wire suspension 8 where it penetrates the housing has no relative motion with the housing because it is anchored thereto. This is unlike pivot bearings that have relative rotation and create wear and blood damage.

Figure 4:
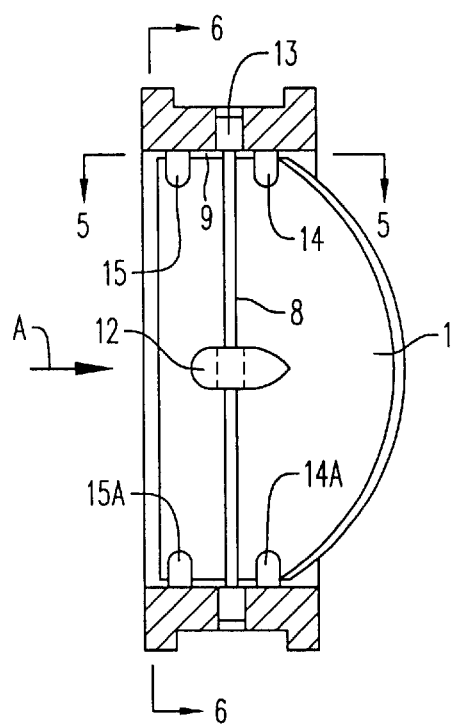
FIG. 4 is a partial section similar to FIG. 1 but with the valve open. It is a view along line 4—4 of FIG. 5.

Referring to FIG. 4, the leaflet socket 12 is shown with a streamlined cross section in the direction of flow to minimize blood turbulence. This can also be done if desired in the top view of the socket in FIG. 5. A gap 10, FIG. 3, is left between the leaflets in their closed position to avoid their contacting.

The wire suspension is designed to be sufficiently stiff so that deflections of the leaflet under inertial and fluid force loading is small compared to the gap sizes used. This is accomplished not only by using a large enough diameter wire, but by installing it preloaded in tension. The outboard fittings 13 may be adhesively bonded into respective sockets 22 in the housing with a tension applied. When the adhesive sets up and becomes rigid, the wire will be left in tension as desired.

To minimize turbulence in the valve, the cross section used for the wire may be a streamlined shape similar to the leaflet socket 12 in the direction of flow. However, due to the small wire size used, typically 0.25 mm diameter, any turbulence using round wire is not excessive because the calculated Reynolds Number for flow past the wire during heart ejection is below 100. This is in the laminar range. Some turbulence is desired for good washout and to minimize blood platelet adhesion.

The ideal mechanical properties of the wire are a low shear modulus of elasticity coupled with a high tensile strength. This combination results in a low induced torsional stress when the leaflet rotates, which is a low percentage of the tensile strength. This ensures that a long fatigue life with high reliability can be achieved.

Flexible polyester fiber in monofilament form is available which meets these requirements better than Kevlar, E-glass, carbon fiber, metals, etc.

Another good synthetic material is high molecular weight polyethylene in the brand name of Spectra fiber. It has a tensile strength greater than hardened steel yet is sufficiently soft or of low modulus that the torsion stress does not get large with a typical leaflet rotation of about 90 degrees.

The hemocompatibility of either material is excellent and both are used in long term blood pumps with excellent non-thrombogenic properties. Carbon coating the wire with Biolite brand carbon is an option to further enhance hemocompatibility if desired.

One of the problems associated with these two materials is securing strong joints with epoxies or other adhesives because the adhesive does not normally adhere well. It is possible to coat these fibers with a coating, such as titanium, in the areas to be bonded. This occurs at the housing and leaflet. In this way the adhesive can be used to directly bond the wire to these structures with the adhesive located between the wire coating and a close fitting hole in the structure.

A preferred method mechanically crimps the fittings 13, 13A onto the wire. The fittings, which can be blood compatible titanium, are adhesively bonded into the housing or leaflet. These fittings 13 and 13A are shown installed on the wire in FIG. 7. The fittings 13, 13A are round or tubular and the wire 8 extends therethrough.

The ends of the fittings 13, 13A exposed to blood are terminated into an integral thin tubular sleeve wall a few thousandths of an inch thick labeled 17. This thin wall portion is squeezed down more than finally desired on the wire using a die. When the die is removed the wire expands elastically and exceeds the yield stress of the thin wall. This expands the sleeve putting it in tension circumferentially. An interface stress is left at the wire outer diameter (O.D.) corresponding to the yield point of the sleeve wall. Thus, just the desired amount of compression stress is left in the wire to firmly secure it and keep fluid out. No adhesive bonding is needed.

Alternatively, the wire can be coated to allow epoxy to adhere for bonding in fittings 13, 13A. Crimping of the sleeve portion 17 is only used as a fluid seal and to resist rotation. The axial preload force is taken by the adhesive.

Figure 8:
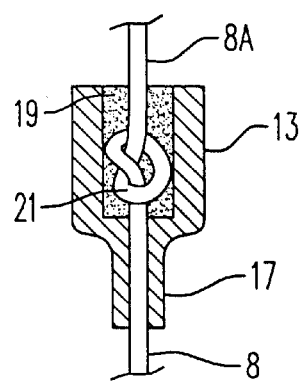
FIG. 8 is a longitudinal section through a fitting of FIG. 7 along line 8—8 enlarged. The wire is not sectioned for clarity.

In yet another embodiment as shown in FIG. 8, a knot 21 is tied in the wire and is located in fitting 13. Epoxy 19 mechanically locks the knot in place. The wire axial preload force is held by the knot so bonding of the epoxy is not relied upon. Sleeve 17 is then crimped to the wire sealing it and eliminating rotation. A knot is used inside central fitting 13A as well.

In all these embodiments, the thin walled sleeve acts as a strain M.G. relief for the wire where it exits because the sleeve can flex being sufficiently thin and long. Since sleeve 17 extends into the fluid, its perimeter is easily washed by the valve blood flow and it does not have to be perfectly round after crimping. A hexagonal or other geometry crimp other than round may be used.

Figure 7:
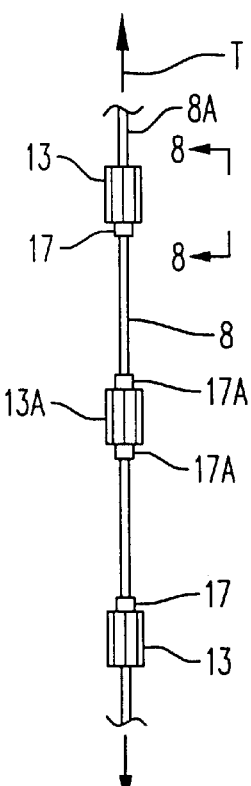
FIG. 7 shows a subassembly of the torsion wire suspension before installation in the valve.

As shown in FIG. 7 excess wire may be initially left overhanging the ends of the two end fittings. These wire ends 8A are used to tension the wire with preload when the fittings are installed in a valve. A jig pulls both ends of the wire to provide the desired preload tension force. When the fitting epoxy dries, the ends of the wire can be trimmed away leaving the wire suspension in tension as desired.

Thus, the use of a thin walled protrusion sleeve 17 on fitting 13 solves the problem of mechanically attaching the fitting to the wire with a controlled compressive stress that makes up for variations in hole size, wire diameter, and degree of squeeze.

The use of pins 14 and 15 as leaflet stops is the only zone of contact in the valve. However, when the leaflet rotates off the stop pins it is completely washed out unlike some M.G. pivot bearings which have integral stops enclosed in the bearing cavity. The cross section of the stops can be streamlined to minimize turbulence of flow past them. The point contact of the stop against the leaflet is so small that blood cell damage is no worse than in pivot bearings. Pin contact stress is also low.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims in which I claim:

What is claimed is:

1. A valve comprising:
   a housing including a pair of sockets;
   a valve leaflet disposed inside said housing and including a socket;
   a torsion wire including a pair of outboard fittings fixedly joined to and surrounding respective outboard ends thereof, and said housing sockets fixedly receive respective ones of said outboard fittings for preventing relative motion therebetween; and
   said torsion wire further including an inboard fitting fixedly joined to and surrounding said wire between said outboard fittings, and said leaflet socket fixedly receives said inboard fitting for suspending said leaflet to said housing for pivotal reciprocation therein.

2. A valve according to claim 1 wherein said leaflet socket is spaced outwardly from said leaflet to provide a gap between said wire and said leaflet.

3. A valve according to claim 1 wherein said outboard fittings are disposed flush with an inner surface of said housing.

4. A valve according to claim 3 wherein said inboard and outboard fittings are adhesively bonded in said respective sockets.

5. A valve according to claim 1 wherein said inboard fitting is centered between said outboard fittings.

6. A valve according to claim 1 wherein said wire is flexible, and is mounted in said housing under tension for effecting a stiff suspension for said leaflet.

7. A valve according to claim 1 wherein said inboard and outboard fittings are tubular, said wire extends therethrough, and is fixedly joined therein.

8. A valve according to claim 7 wherein said inboard and outboard fittings are mechanically crimped to said wire for being fixedly joined thereto.

9. A valve according to claim 8 wherein said inboard and outboard fittings include integral sleeves extending therefrom and surrounding said wire to effect fluid seals thereat.

10. A valve according to claim 9 wherein said sleeves are mechanically crimped to said wire for sealing therewith.

11. A valve according to claim 7 wherein said inboard and outboard fittings are adhesively bonded to said wire for being fixedly joined thereto.

12. A valve according to claim 11 wherein said inboard and outboard fittings include integral sleeves extending therefrom and surrounding said wire to effect fluid seals thereat.

13. A valve according to claim 12 wherein said sleeves are mechanically crimped to said wire for sealing therewith.

14. A valve according to claim 7 wherein said wire includes a knot in respective ones of said inboard and outboard fittings.

15. A valve according to claim 7 wherein said wire is a synthetic fiber, and said fittings are metal.

16. A valve according to claim 7 wherein said wire is round, with a diameter of about 0.25 mm.

17. A valve according to claim 7 further comprising a pair of said leaflets mounted in said housing by respective ones of said torsion wires and corresponding fittings in a common plane having gaps between said leaflets and housing.

18. A valve according to claim 17 further comprising a plurality of stop pins fixedly mounted inside said housing for abutting said leaflets to limit pivotal movement thereof between open and closed positions.

19. A valve according to claim 18 wherein two of said stop pins have a line of centers therebetween passing through a centroid of said leaflet in said closed position.

20. A valve according to claim 12 wherein said sleeves are thinner than said inboard and outboard fittings to provide strain relief for said torsion wire thereat.

* * * * *